United States Patent
Krizan et al.

(10) Patent No.: US 11,266,568 B2
(45) Date of Patent: Mar. 8, 2022

(54) ELASTOMER COMPONENTS CONTAINING TAGGANTS

(71) Applicant: West Pharmaceutical Services, Inc., Exton, PA (US)

(72) Inventors: Jason Krizan, Ellicott City, MD (US); Michael Sullivan, Birdsboro, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 17/272,897

(22) PCT Filed: Sep. 9, 2019

(86) PCT No.: PCT/US2019/050186
§ 371 (c)(1),
(2) Date: Mar. 2, 2021

(87) PCT Pub. No.: WO2020/055737
PCT Pub. Date: Mar. 19, 2020

(65) Prior Publication Data
US 2021/0212896 A1    Jul. 15, 2021

Related U.S. Application Data

(60) Provisional application No. 62/729,814, filed on Sep. 11, 2018.

(51) Int. Cl.
*A61J 1/14*    (2006.01)
*A61M 5/315*    (2006.01)
*A61M 5/32*    (2006.01)

(52) U.S. Cl.
CPC .......... *A61J 1/1468* (2015.05); *A61J 1/1412* (2013.01); *A61M 5/31511* (2013.01);
(Continued)

(58) Field of Classification Search
CPC .... A61J 1/1412; A61J 1/1468; A61J 2205/00; A61J 2205/30; A61J 2205/60; A61M 5/31511; A61M 5/3202; A61L 31/128
See application file for complete search history.

(56) References Cited

U.S. PATENT DOCUMENTS 4,256,038 A    3/1981    Dietz et al.
4,652,395 A    3/1987    Marcina et al.
(Continued)

FOREIGN PATENT DOCUMENTS

CN    1926029 A    3/2007
CN    105228690 A    1/2016
(Continued)

OTHER PUBLICATIONS

International Preliminary Report on Patentability dated Feb. 16, 2021 in In'tl Application No. PCT/US2019/050186.
(Continued)

*Primary Examiner* — Brandy S Lee
(74) *Attorney, Agent, or Firm* — BakerHostetler

(57) ABSTRACT

A medical component is provided which includes a first portion formed of a first elastomeric material having at least one taggant embedded or incorporated therein, and a second portion formed of a second elastomeric material. The at least one taggant has a first diffusivity relative to the first elastomeric material and a second diffusivity relative to the second elastomeric material. The second diffusivity is less than the first diffusivity.

15 Claims, 6 Drawing Sheets

(52) U.S. Cl.
CPC ........ *A61M 5/3202* (2013.01); *A61J 2205/00* (2013.01); *A61J 2205/60* (2013.01)

(56) References Cited

U.S. PATENT DOCUMENTS

| | | | |
|---|---|---|---|
| 5,362,568 | A | 11/1994 | Dietz et al. |
| 5,888,424 | A | 3/1999 | Ebnesajjad et al. |
| 2005/0189255 | A1 | 9/2005 | Safian |
| 2010/0056688 | A1 | 3/2010 | Greer et al. |
| 2011/0100091 | A1* | 5/2011 | Harrup ................ C08G 79/025 73/23.35 |
| 2015/0165125 | A1 | 6/2015 | Foucher et al. |
| 2015/0299851 | A1 | 10/2015 | Bicker et al. |
| 2016/0022918 | A1 | 1/2016 | Gunzel |
| 2017/0152372 | A1 | 6/2017 | Quittmann et al. |

FOREIGN PATENT DOCUMENTS

| | | |
|---|---|---|
| EP | 0482577 A2 | 4/1992 |
| EP | 1060031 B2 | 12/2000 |
| EP | 2095836 A1 | 9/2009 |
| EP | 3028730 A1 | 6/2016 |
| JP | 2003-037730 A | 2/2003 |
| JP | 2015-507028 A | 3/2015 |
| JP | 2015-062564 A | 4/2015 |
| WO | 03006083 A2 | 1/2003 |
| WO | 2011059823 A1 | 5/2011 |
| WO | 2013115331 A1 | 8/2013 |
| WO | 2014169977 A1 | 10/2014 |
| WO | 2014194918 A1 | 12/2014 |

OTHER PUBLICATIONS

Office Action dated Jun. 4, 2021 in Chinese Application No. 201980059118.2.
West Pharmaceutical Services Introduces West FluroTec Barrier Film; State-of-the-Art Parenteral Packaging Technology May Reduce Risk of Costly Drug Contamination, Oct. 27, 2003.
Rodriguez et al., "Role of hydrophobicity on interfacial fluid flow: Theory and some application", The European Physical Journal. E, 37:57, 14 pages (Jun. 2014).
Written Opinion of the IPEA dated Dec. 17, 2020 in Int'l Application No. PCT/US2019/050186.

* cited by examiner

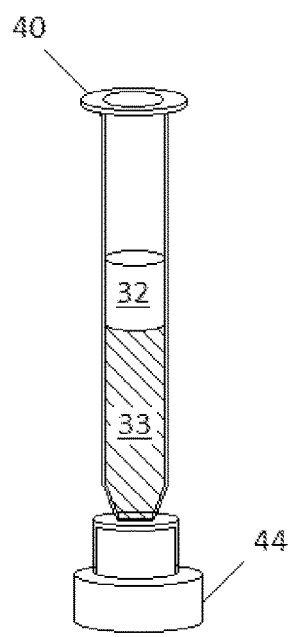
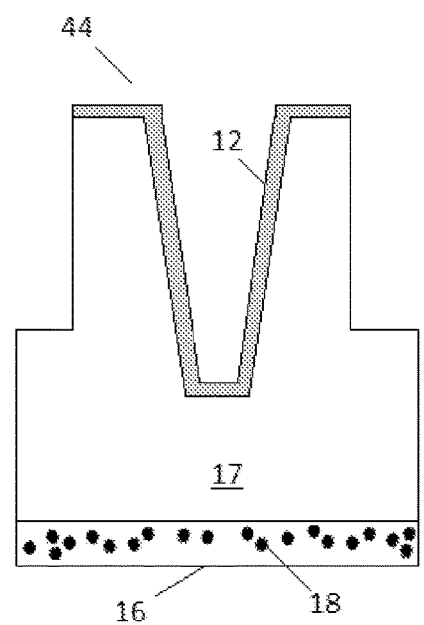
Fig. 4A
Fig. 4B
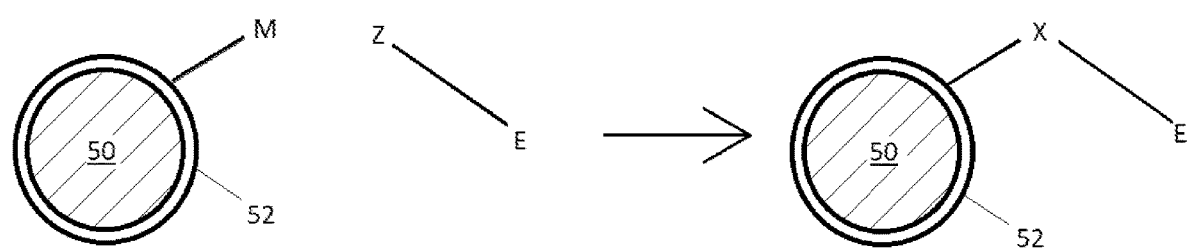
Fig. 5

ELASTOMER COMPONENTS CONTAINING TAGGANTS

CROSS-REFERENCE TO RELATED APPLICATIONS

This application is a section 371 of International Application PCT/US2019/050186, filed Sep. 9, 2019, which was published on Mar. 19, 2020 under Publication No. WO 2020/055737 A1, and which claims the benefit of and priority to U.S. Provisional Application having Ser. No. 62/729,814 filed on Sep. 11, 2018. The entire contents of these applications are incorporated herein by reference in their entirety.

BACKGROUND OF THE INVENTION

Various embodiments of the present invention are directed to elastomeric components containing taggants, and more specifically, elastomers containing taggants that are used to manufacture components, such as stoppers, plungers, needle shields, and tip caps, for medical devices, particularly containment systems.

In order to prevent counterfeiting of manufactured goods, particularly in the field of medical devices, labels and product packaging may be provided with some indicia or other recognizable characteristic to identify the source or confirm the origin of the goods. However, few attempts have been made to provide the individual components within an assembled product with some recognizable indicia or property.

Because prior attempts utilize whole-package solutions, i.e. fully assembled and packaged products, they are not able to identify counterfeits earlier in the manufacturing process associated with the individual components forming part of the assembled product. Thus, there is a need for improved components and methods of providing components with anti-counterfeit features, such that the source of the components may be confirmed prior to their use in manufactured goods.

BRIEF SUMMARY OF THE INVENTION

In one aspect, the present invention relates to a medical component comprising a first portion including at least one taggant and a first elastomeric material, and a second portion comprising a second elastomeric material. The at least one taggant has a first diffusivity relative to the first elastomeric material and a second diffusivity relative to the second elastomeric material, and the second diffusivity is less than the first diffusivity.

In another aspect, the present invention relates to a medical component comprising an elastomer containing at least one taggant and a barrier film provided on at least a portion of a surface of the medical component. The barrier film has an average pore size and the at least one taggant has an average particle size which is greater than the average pore size of the barrier film.

In another aspect, the present invention relates to a method of manufacturing a medical component. The method comprises preparing a first sheet of an elastomeric material, preparing a mold by applying a fluid containing one or more taggants to the mold, and arranging the first sheet in the prepared mold and molding the first sheet therein to cure the elastomeric material and form the medical component. The taggants of the fluid thereby become incorporated into the medical component.

In another aspect, the present invention relates to another method of manufacturing a medical component. The method comprises preparing a first sheet of an elastomeric material, preparing a barrier layer to be applied to at least a portion of the first sheet, applying a fluid containing one or more taggants to a first surface of the first sheet or to a first surface of the barrier layer, and arranging the first sheet and the barrier layer in a mold, such that a second surface of the barrier layer is in contact with the mold and the first surface of the barrier layer is in contact with the first surface of the first sheet, and molding the first sheet therein to cure the elastomeric material and form the medical component. The one or more taggants of the fluid thereby become incorporated into the cured elastomeric material.

In another aspect, the present invention relates to another method of manufacturing a medical component. The method comprises at least partially molding a first portion of the medical component from a first elastomeric material including at least one taggant incorporated therein or thereon, overmolding the first portion with a second elastomeric material which is devoid of any taggants, and curing the first and second elastomeric materials to form the medical component.

These and other aspects of the present invention will be apparent in view of the following description.

BRIEF DESCRIPTION OF THE SEVERAL VIEWS OF THE DRAWINGS

Various aspects and embodiments of the application will be described with reference to the following figures. It should be appreciated that the figures are not necessarily drawn to scale. The figures depict one or more implementations in accord with the present concepts, by way of example only, not by way of limitations. In the figures, like reference numerals refer to the same or similar elements.

FIG. 4A is a top perspective view of a pre-filled luer lock syringe including a tip cap comprising an elastomeric material according to yet another embodiment of the present invention;

FIG. 4B is a cross-sectional side view of a schematic representation of the tip cap illustrated in FIG. 4A;

FIG. 5 is a schematic illustration of a taggant covalently bonding to a polymer of an elastomeric material according to another embodiment of the present invention;

DETAILED DESCRIPTION OF THE INVENTION

Figure 1:
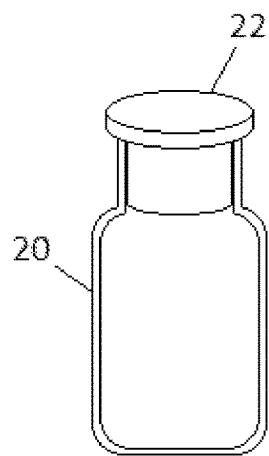
FIG. 1 is a top perspective view of a vial including a stopper comprising an elastomeric material according to an embodiment of the present invention.

Generally, the various embodiments of the present invention are directed to a polymeric composition, and more particularly an elastomeric composition, containing one or more types of taggants. Each taggant may be positively identified by its physical or chemical properties. The elastomeric composition is preferably used to manufacture components of medical devices, particularly elastomeric components, such as elastomeric stoppers, caps, plungers, needle shields, needle caps, syringe cartridges, vials, and the like. Preferably, the taggants are provided at or proximate a surface of the elastomeric component. Positive identification of the taggants contained in the elastomeric composition of the medical component enables determination of the origin of the component, and thereby, prevents the use of counterfeit components early in the supply chain of medical devices, particularly closure assemblies, such as vials and syringes. Similarly, it is beneficial to the patient/caregiver to prevent counterfeit elastomers/seals from being used to re-seal original vials with fake or adulterated drug product.

Examples of the elastomeric material that may be used include, but are not limited to, polyisoprene; polybutadiene; styrene-butadiene copolymers; ethylene-propylene copolymers; ethylene-propylene-diene copolymers; chlorosulphonated polyethylene; ethylene-vinyl acetate copolymer; styrene-isoprene copolymers; fluroelastomers such as FKM, perfluoro-elastomers (FFKM) and tetrafluoro ethylene/propylene rubbers (FEPM); synthetic or natural rubbers, such as butyl rubber, isoprene rubber, butadiene rubber, halogenated butyl rubber (e.g., bromobutyl rubber), ethylene propylene terpolymer, silicone rubber; combinations thereof and the like. Preferably, the elastomeric material is a butyl or halobutyl elastomer. The elastomeric material may further comprise one or more additives such as a vulcanizing agent, a vulcanizing accelerator, a vulcanizing activator, a processing aid, a filler, and a reinforcing agent to improve or enhance the properties of the elastomeric material.

The one or more taggants included in or applied to the elastomeric materials, according to the various embodiments of the present invention, may be selected from a variety of materials having one or more identifiable properties. Such properties include, but are not limited to, size, particle size distribution, shape, particle shape distribution, color, and chemical composition specifically as a result of isotopic enrichment/labeling. For example, hydrothermally synthesized crystalline materials are difficult to produce and are known to have a narrow particle size distribution. Therefore, the incorporation of such crystalline materials in an elastomeric matrix as the taggant would allow the particle size distribution of the crystalline taggant to be used as an unique identifier for the elastomeric material.

Examples of the taggants that may be incorporated or applied to the elastomeric component, according to embodiments of the present invention, include, but are not limited to, ceramic materials including, but not limited to, ceramics doped with rare earth metals; hydrocarbon or fluorocarbon oil for spectroscopic (e.g., infrared or UV-Vis) detections; fluorescent organic or inorganic compounds for spectroscopic (e.g., infrared or UV-Vis) detection; magnetic materials, such as ferromagnetic ceramics and low coercivity materials; surface functionalized particulates; and composite particles (e.g. ceramic cores having an organic or reactive shell). In some embodiments, the taggants may include RFID microchips.

In one preferred embodiment of the present invention, the taggants are ceramic taggants distinguishable by their size, shape, or spectral properties. In another preferred embodiment of the present invention, the taggants are fillers for elastomeric materials which have unique isotopic ratios. Examples of such fillers are deuterated organic molecules and ceramics containing enriched boron. In another embodiment of the present invention, a plurality of taggants in various concentrations are incorporated into the elastomeric matrix, which increases the complexity of the make-up of the elastomeric matrix and renders it more difficult to manufacture a counterfeit component or tamper with the tagged elastomeric component. The implementation of a taggant on or in an elastomer component to be used with a containment system (e.g., a syringe or vial), would also enable tracing of the elastomer component back to a particular lot.

In other embodiments of the present invention, the taggants comprise filler materials that are typically included in the elastomeric matrices used to form medical components, but the filler materials have been pretreated in a manner that provides them with a unique identity. For example, at least a portion of the filler materials may be surface functionalized or isotopically enriched so as to provide the fillers with a unique chemical composition and/or concentration that may be determined by an analytical method, such as mass, infrared, or Raman spectroscopy. Surface functionalization of the filler materials may also enable the modified filler materials to be more easily incorporated in the elastomeric matrix.

For example, with reference to FIG. 5, a taggant particle 50 may include a functional group M on its surface or alternatively, the taggant particle 50 may be coated with a shell 52 having the functional group M on its surface. The functional group M may readily react with a corresponding functional group Z of an elastomeric material E to form a covalent bond. As would be known to those of skill in the art, the functional group M and Z may be selected from a variety of reactive pairs (e.g., hydroxyl groups, a carboxylic acids, vinyl groups, halogenated compounds and epoxide groups). Alternatively, the functional groups M and Z may include a polymerizable group (e.g., an acrylate, methacrylate, styryl, or other vinyl group), so that the surface of the taggant may be co-polymerized with the elastomer.

As previously mentioned, the elastomeric components made according to the various embodiments of the present invention are preferably provided in the form a vial stopper, syringe plunger, needle shield, tip cap or container cap/seal (such as a flip-off cap for a vial). It will be understood that the present invention is not limited to such forms, and may include any medical component, for example, a cartridge piston (plunger, stopper or closure), a syringe piston (plunger, stopper or closure), a vial piston (plunger, stopper or closure), a seal, a gasket, a component of a pre-filled syringe, a sleeve or container stopper, a flashback bulb, a cap, a liner, a washer, or any other component/device which may be in contact with pharmaceutically pure materials or medicament.

In a preferred embodiment, the pharmaceutical medicament with which the elastomeric component may be used is insulin (or any derivative, formulation or analog thereof). For example, as used herein, the term "insulin" shall mean insulin, insulin analogs, insulin derivatives or mixtures thereof, including human insulin or a human insulin analogs or derivatives. Examples of insulin analogs include, but are not limited to, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives include, but are not limited to, B29-N-myristoyl-des(B30) human insulin; B29-N-palmitoyl-des(B30) human insulin; B29-N-myristoyl human insulin; B29-Npalmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N(N-palmitoyl-Y-glutamyl)-des(B30) human insulin; B29-N(N-lithocholyl-Y-glutamyl)-des(B30) human insulin; B29-N-(w-carboxyheptadecanoyl)-des(B30) human insulin and B29-N-(w-carboxyheptadecanoyl) human insulin. Generally, the pharmaceutical medicament with which the elastomeric component may be any high value biologic or personalized injectable drug, particularly any parenteral application of medicament.

Figure 2A:
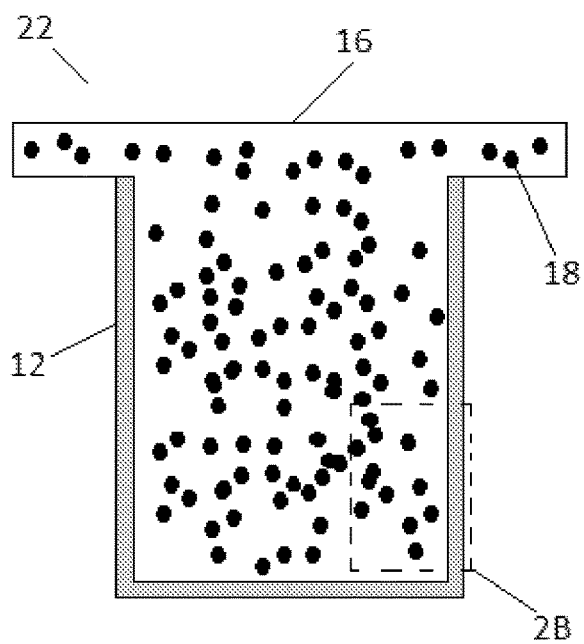
FIG. 2A is a cross-sectional side view of a schematic representation of the stopper illustrated in FIG. 1.
Figure 2B:
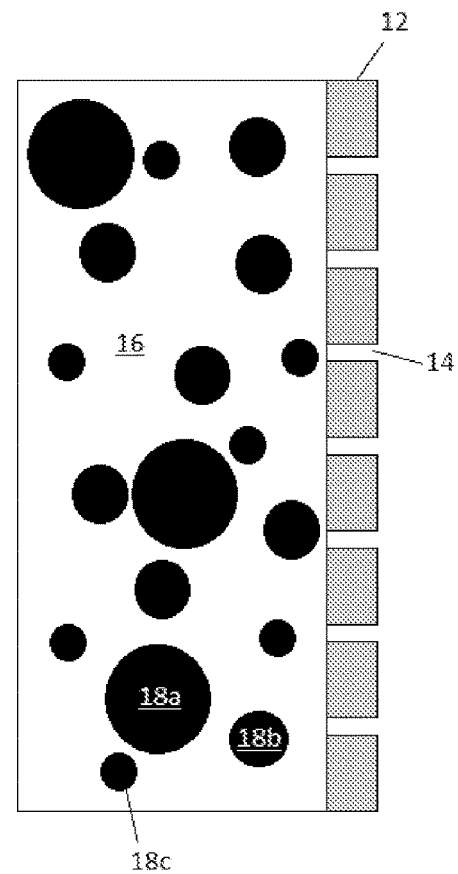
FIG. 2B is a magnified view of the area 2B of FIG. 2A.

Referring to FIGS. 1, 2A, and 2B, an elastomeric component 22 according to one embodiment of the present invention is illustrated. The elastomeric component 22 is in the form of a stopper and is shown inserted in the opening of a vial 20. The component 22 comprises an elastomeric material 16 and a plurality of taggant particles 18a, 18b, 18c (hereinafter collectively referred to as taggants 18) incorporated in or applied to the elastomeric material. In a preferred embodiment, the elastomeric material 16 forms the continuous phase of an elastomeric matrix, while the taggants 18 form the discontinuous phase of the elastomeric matrix. It will be understood by those skilled in the art that the taggant particles 18a, 18b, 18c shown in FIG. 2B may be of a single type or a plurality of different types. The taggants 18 are preferably embedded in the elastomeric component at least at or near its surface, but may also be embedded in the elastomeric component throughout its body.

In one embodiment, the elastomeric component 22 preferably further comprises a barrier layer 12 that is applied to at least a portion of an exterior surface of the component 22. Preferably, the barrier layer 12 is applied to portions of the exterior surface of the elastomeric component 22 that are configured to occupy the internal space of the vial 20 where there is high likelihood of contact with the products contained in the vial 20. The barrier layer is preferably configured to prevent or at least reduce the risk of the potential diffusion of the taggants from the elastomeric matrix of the component 22 and into the contents of the vial 20. Where the contents of the vial 20 are a pharmaceutical drug product, for example, interaction between the taggant and pharmaceutical drug is undesired, as the taggant may have an impact on the safety and/or efficacy of the pharmaceutical drug. Preventing contact between the taggant and pharmaceutical drug product is especially critical for pharmaceuticals intended for subcutaneous or intravenous injection into a human or animal.

Referring to FIG. 2B, the barrier layer 12 may be configured, such that the one or more taggants 18a, 18b, 18c are insoluble in the materials of the barrier layer 12. In one embodiment, the barrier layer 12 is continuous and/or non-porous. In another embodiment, the barrier layer 12 comprises a plurality of pores 14. The average diameter of the pores 14 is set to a size that is less than the average particle diameter of the one or more taggants 18a, 18b, 18c, thereby providing a physical obstacle preventing the transmission of taggants 18 across the barrier layer 12. Particle size can be determined through a variety of known microscopy techniques or dynamic light scattering depending on the size of the particles. The average pore diameter of the barrier layer may be greater than or equal to 75 nm and less than or equal to 20 µm. However, it will be understood by those skilled in the art that a barrier layer 12 having appropriate pore sizes will be selected depending upon the specific taggants 18 incorporated into the elastomer.

The barrier layer 12 comprises one or more polymers. In a preferred embodiment, the barrier film 12 is a fluoropolymer film. Fluoropolymers are readily known in the art and a detailed description of them is not necessary for a complete understanding of the present invention. Exemplary fluoropolymers include, but are not limited to, polytetrafluoroethylene (PTFE), ethylene tetrafluoroethylene (ETFE), homopolymers and copolymers of tetrafluoroethylene (TFE), perfluoroalkoxy polymer resin (PFA), copolymers of hexafluoropropylene and tetrafluoroethylene, polyethylenetetrafluoroethylene (PETFE), polyvinyl fluoride (PVF), fluorinated ethylenepropylene copolymers (FEP), polyethylenechlorotrifluoroethylene (PECTFE), polyvinylidene fluoride (PVDF), polychlorotrifluoroethylene, (PCTFE), and derivatives thereof. Preferably, the barrier film 12 is formed of PTFE or ETFE.

All of the elastomeric components described herein, including the above-described elastomeric component 22, are preferably formed by a molding process. For all of the embodiments disclosed herein, the time, heat and pressure for each molding step will depend upon various factors, such as the specific elastomeric material and taggants being used and whether the desired result is partial curing of the elastomeric material or full curing of the elastomeric material. Such elastomeric materials and molding processes (e.g., compression molding, injection molding, overmolding, and the like) are well known in the art and a detailed description of each molding step time, temperature and pressure specifications is not necessary for a complete understanding of the present invention. For example, each molding step for the embodiments disclosed herein is conducted preferably at temperatures of about 120 to 310° C. and pressures of about 40 to 350 kg/cm$^2$ for a few seconds (e.g., less than 10 seconds) to 30 minutes, and more preferably about 120 to 220° C. and pressures of about 40 to 70 kg/cm$^2$ for about 30 seconds to 30 minutes, and most preferably at temperatures of about 140 to 220° C. and pressures of about 40 to 70 kg/cm$^2$ for about 2 to 15 minutes.

Figure 6:
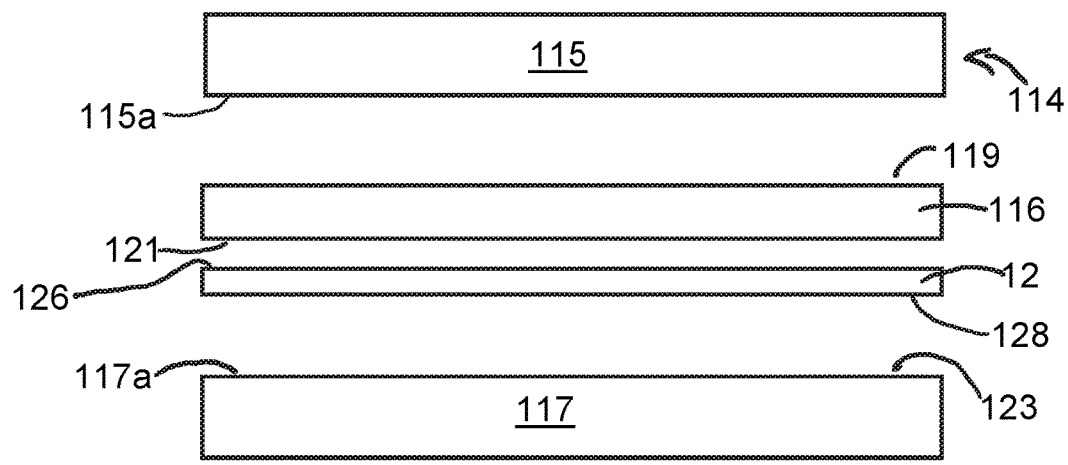
FIG. 6 depicts a one-step molding process in accordance with an embodiment of the present invention.

Referring to FIG. 6, there is shown an embodiment of a method of manufacturing the medical component utilizing a mold 114 and an elastomer sheet 116 in a one-step molding process, and more particularly in a one-step compression molding process. It will be understood by those skilled in the art that the mold 114 is not limited to the configuration shown in FIG. 6, but rather may have any configuration and dimensions as necessary to achieve the desired finished elastomeric component, be it a vial stopper, syringe piston, needle shield, tip cap, cap, and the like.

Referring to FIG. 6, the mold 114 includes an upper mold half 115 having an open cavity 115a and a lower mold half 117 having an open cavity 117a. Each cavity 115a, 117a is preferably an open heated mold cavity 115. In a preferred embodiment, the mold 114 includes a plurality of upper and lower mold halves 115, 117 and respective cavities 115a, 117a arranged in an array. In the embodiment of FIG. 6, the bottom surface of the mold cavity 117a of the lower mold half 117 defines a planar surface 123. The planar surface 123 also corresponds to the interior bottom surface of the lower mold half 117.

The elastomer sheet 116 is preferably formed of one or more elastomeric materials (i.e., one or more of the elastomeric materials described above) in a partially cured stage. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes. As such, the elastomer sheet 116 is essentially an elastomer preform. The elastomer sheet 116 has a first surface 119 and an opposing second surface 121.

In a preferred embodiment, a liquid slurry, suspension or solution (hereinafter referred to as a "taggant fluid" for brevity) containing the taggant or taggants to be incorporated into the elastomeric material is first formed. The taggant fluid is preferably sufficiently clean as to be able to maintain the cleanliness of the finished elastomeric component. For example, the taggant fluid should not leave any residue capable of causing a pH shift, should not leave reducing substances, and should not increase extractables/leachables from the finished elastomeric component. Preferably, the taggant or taggants are dispersed in pure water to form the taggant fluid, and the water completely dissipates prior to molding. Other generally safe solvents that could be fully volatilized prior to molding and would also be satisfactory include, but are not limited to, low molecular weight silicone, ethanol, isopropyl alcohol, or heptanes. Surfactants, such as polysorbates (i.e. polysorbate 20), may also be incorporated in the taggant fluid to assist with dispersion.

In one embodiment, the one or more taggants or taggant fluid is incorporated directly into the elastomeric matrix or composition used to form the elastomer sheet 116. In another embodiment, the taggant fluid is applied either directly onto the elastomeric sheet 116, onto the barrier film 12, or into the mold 114. By doing so, the taggants are embedded on and/or near the surface of the molded component. Preferably, the taggant fluid is applied by spraying. The spraying action may be performed using the same technology used for paint spraying, either airless or using compressed air (e.g., <60 psi). By spraying the mold 114 with the taggant fluid, a more even application of the taggants may be achieved. It will be understood by those skilled in the art that precise spray conditions will be dependent on the types of taggants being used, as well as other properties of the taggant fluid (e.g., viscosity).

It will be understood by those skilled in the art that application of the taggant fluid need not be done by spraying, but rather may be done by any of a variety of known coating methods. For example, the taggant fluid may be applied by painting (e.g., using contact with a brush), dip coating (e.g., in either a solution/dispersion or by bringing in contact with dry powder), deposition process, or sublimation.

In the manufacturing method according to the embodiment of FIG. 6, which utilizes a barrier film 12, the elastomer sheet 116 and barrier film 12 are positioned over the lower mold half 117. In the assembled position, one surface 128 of the barrier film 12 is in contact, and more particularly, direct contact with the planar surface 123. As discussed above, one or more taggants or the taggant fluid may have been incorporated into the elastomeric matrix used to form the elastomer sheet 116. Alternatively, and preferably, the taggant fluid is applied (e.g., by spraying) onto either the first surface 119 or the second surface 121 of the elastomer sheet 116 or onto a surface 126 of the barrier film 12 which is configured to contact the second surface 121 of the elastomer sheet. The assembly is then given a predetermined time for the taggant fluid to dry, such that all or virtually all of the carrier liquid/solvent is dissipated prior to molding. For example, the assembly may be rested for a duration of from approximately 0.05 seconds to 900 seconds, preferably approximately 1 to 60 seconds, in order to allow the taggant fluid to dry. The drying process may be facilitated by any known drying mechanism or method. In a preferred embodiment, the taggant fluid is applied to the barrier film 12, so as to avoid trapping any liquid in the elastomer surface texture.

The assembly is then subjected to compression molding to fully cure the elastomeric material. More particularly, the mold 114 is closed such that each upper mold half 115 covers each respective lower mold half 117, and heat and pressure are applied to cause the elastomeric material of the elastomer sheet 116 to flow, thereby forcing the flowing elastomeric material into contact with all areas of each mold cavity 115a, 117a until the elastomeric material has cured to form the medical component 22.

The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

In one embodiment (not shown), the barrier film 12 is not utilized in the method of FIG. 6. In such an embodiment, the taggant fluid may be incorporated into the elastomer matrix, or may be applied directly onto the surface 121 of the elastomer sheet 116, or applied directly to the mold 114. Preferably, where no barrier film is used, the taggant fluid is applied to the mold 114. The taggant fluid may be applied (e.g., sprayed) onto the mold cavities 115a, 117a after an earlier application of a mold release solution. Alternatively, the taggant fluid may be incorporated into the mold release solution, which is then applied (e.g., by spraying) onto the mold cavities 115a, 117a.

Figure 2C:
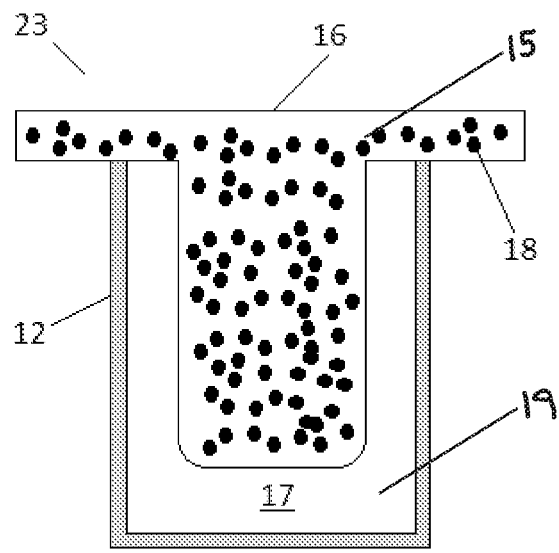
FIG. 2C is a cross-sectional side view of a schematic representation of a stopper according to another embodiment of the present invention.

In another embodiment of the present invention, illustrated in FIG. 2C, the elastomeric component 23 comprises a first portion 15 comprising a first elastomeric material 16 including at least one type of taggant 18 incorporated therein, and a second portion 19 comprising a second elastomeric material 17 which is devoid of any taggants. The second portion 19 is preferably configured to cover at least a portion of the first portion 15, such that the second portion 19 serves as a barrier between the tagged first portion 15 and any pharmaceutical drug product within a container using the component. Therefore, the exterior surface of the second portion 19 preferably forms the surface(s) of the elastomeric component 23 likely to contact a pharmaceutical drug product when installed in a container. It will be understood that while the elastomeric component 23 shown in FIG. 2C is in the form of a vial stopper, the component may take any of the forms mentioned above (e.g., caps, plungers, needle shields, needle caps, syringe cartridges, vials, and the like).

In a preferred embodiment, the second elastomeric material 17 is selected such that the rate of diffusion, i.e. diffusivity, of the taggant 18 through the second elastomeric material 17 is less, i.e. slower, than the rate of diffusion of the taggant 18 through the first elastomeric material 16. By incorporating the taggant 18 within the first portion 15 of the elastomeric component 23, which is remote from the product contact surface, and by including the second portion 19 of the elastomeric component 23 to surround or cover the tagged first portion 15, the likelihood of any product interaction with the taggants may be reduced or eliminated. In such a configuration, a barrier layer 12 may or may not be applied to the outer surface of the second portion 19.

The elastomer component 23 may be manufactured by compounding the first elastomeric material 16 with one or more taggants 18 and molding the first portion 15. The molded first portion 15 may then be overmolded with the second elastomeric material 17 of the second portion 19 to form the final component 23. Alternatively, the two portions 15, 19 may be separately molded and the joined together to form the finished elastomer component 23. Optionally, a barrier film 12 may be applied to the outer surfaces of the second portion 19 below the flange portion of the stopper 23.

Figure 7:
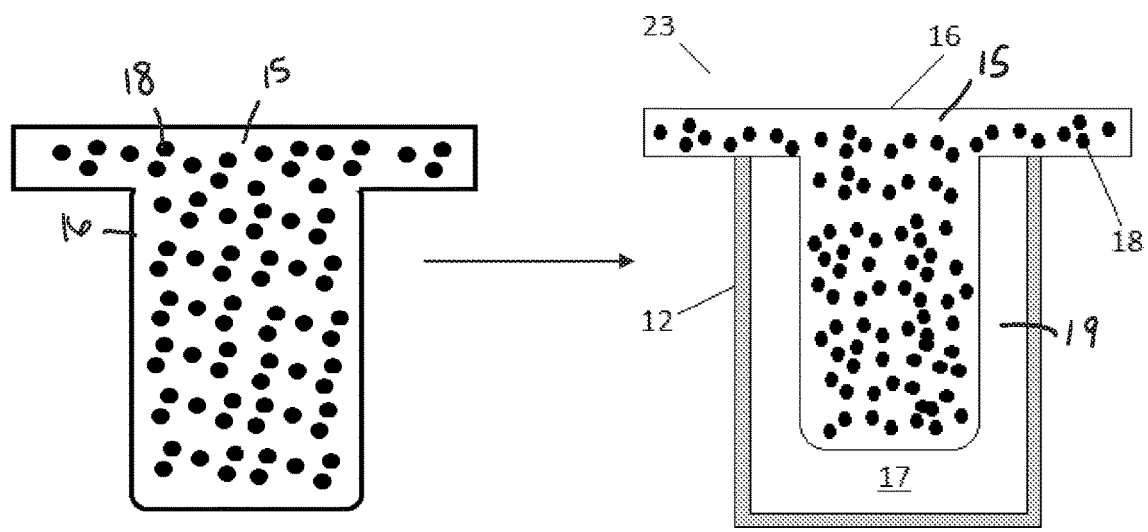
FIG. 7 depicts a two-step molding process in accordance with another embodiment of the present invention.
Figure 8:
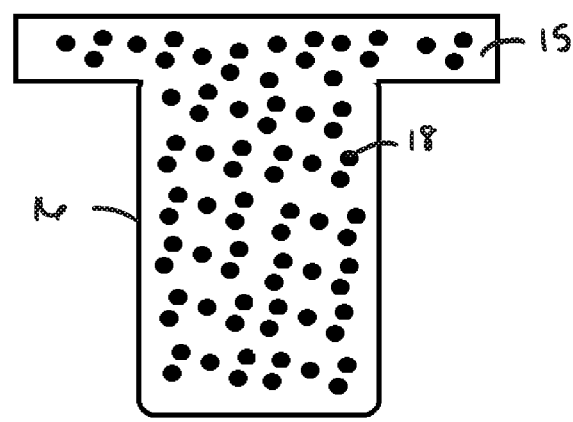
FIG. 8 depicts a two-step molding process in accordance with another embodiment of the present invention.
Figure 8:
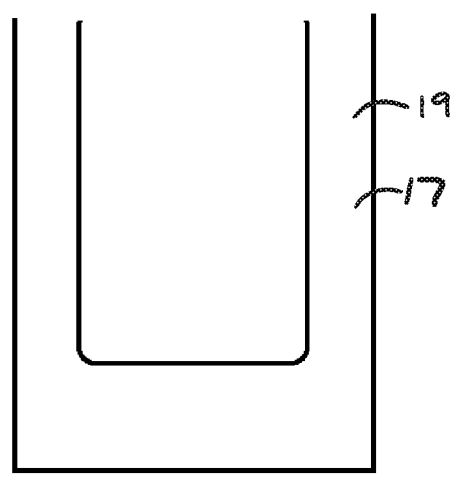

For example, an elastomeric component formed of two different elastomer materials, such as the elastomer component 23 of FIG. 2C, may be formed by a two-step molding process as follows. Referring to FIGS. 7-8, there are shown further embodiments of methods of manufacturing the elastomeric component in a two-step molding process. In FIG. 7-8, the elastomeric component is depicted as a vial stopper for exemplary purposes, and particularly the vial stopper 23 shown in FIG. 2C, but it will be understood that all of the methods discussed herein could be used to form any medical component.

Referring to FIG. 7, the method comprises forming the first portion 15 of the vial stopper 23 by molding of the first elastomeric material 16. The first portion 15 including the taggants 18 is preferably formed by the molding process described above with respect to FIG. 6. That is, the taggant or taggant fluid is either incorporated into the elastomer matrix, applied directly onto the surface 121 of the elastomer sheet 116, applied directly to the mold 114 after an earlier application of a mold release solution, or incorporated into a mold release solution which is applied to the mold, and the elastomer sheet 116 is then subjected to compression molding to form the first portion 15, preferably in a partially cured state. The process conditions for this molding step are 120 to 310° C. or higher and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Then, in a second molding step, the second elastomeric material 17 is overmolded onto the first portion 15, and cured to form the finished elastomeric component. The process conditions for this second molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

In another embodiment, as shown in FIG. 8, instead of an overmolding process, the first portion 15 and second portion 19 are first separately formed by any known molding method, under predetermined time, heat and pressure conditions as discussed herein, in partially cured states. The process conditions for these molding steps are 120 to 310° C. and about 40 to 350 kg/cm² for a few seconds to 30 minutes, more preferably about 120 to 70° C. and about 40 to 220 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Next, the second portion 19 is assembled with the first portion 15 in a mold, such that the portions 15, 19 contact each other at an interface, and the assembled first and second portions 15, 19 are bonded or welded together by heating the entire assembly in the mold to fully cure the first and second elastomeric material 16, 17 under predetermined time, heat and pressure conditions. The process conditions for this molding step are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Alternatively, in accordance with another embodiment, a localized curing process may be implemented. More particularly, the first and second portions 15, 19 may be initially molded in a fully cured state. The process conditions for these molding steps are 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Next, the first and second portions 15, 19 are assembled as discussed above, and bonded or welded together at the interface by a directed energy source, such as, but not limited to, ultrasonic welding, microwave heating/curing, and laser heating/curing, that effects localized curing the first and second elastomeric materials 16, 17 at the interface.

The process conditions for this localized curing step is 120 to 310° C. and about 40 to 350 kg/cm² for a few seconds to 30 minutes, more preferably about 120 to 220° C. and about 40 to 70 kg/cm² for about 30 seconds to 30 minutes, and most preferably about 140 to 220° C. and about 40 to 70 kg/cm² for about 2 to 15 minutes. In one embodiment, the process conditions are 150 to 175° C. and 40 to 70 kg/cm² for about 10 minutes. In another embodiment, the process conditions are 160 to 165° C. and about 50 kg/cm² for about 15 minutes. In another embodiment, the process conditions are 160 to 175° C. and 40 to 70 kg/cm² for about 8 minutes.

Figure 3A:
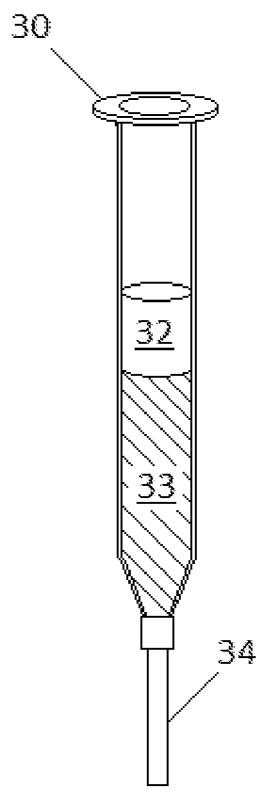
FIG. 3A is a top perspective view of a pre-filled syringe including a plunger and needle shield comprising an elastomeric material according to another embodiment of the present invention.
Figure 3B:
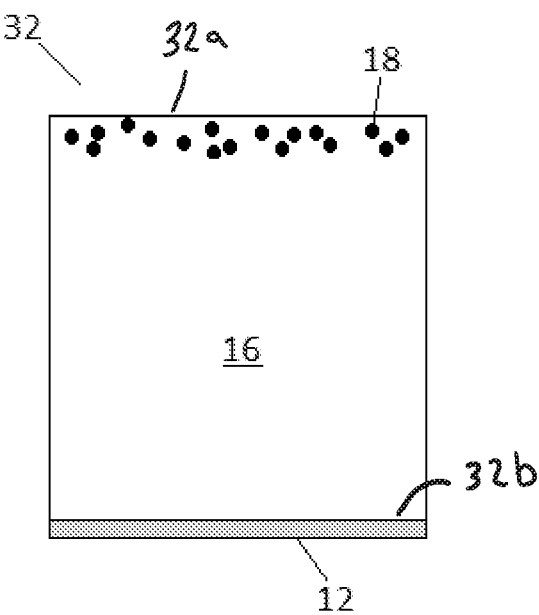
FIG. 3B is a cross-sectional side view of a schematic representation of the plunger illustrated in FIG. 3A.
Figure 3C:
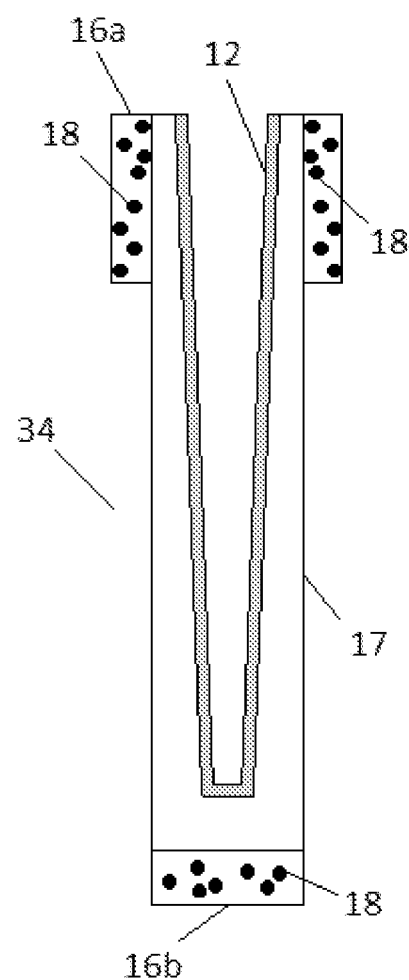
FIG. 3C is a cross-sectional side view of a schematic representation of the needle shield illustrated in FIG. 3A.

In another embodiment, referring to FIGS. 3A, 3B, and 3C, a pre-filled syringe 30 containing a drug product 33 includes a plunger 32 and a needle shield 34. The plunger 32 may include an elastomeric material 16 containing one or more taggants 18. The plunger 32 may be configured such that the one or more taggants 18 are concentrated at first end 32a of the plunger 32. The first end 32a of the plunger 32 is preferably located distally relative to the drug product 33 when the plunger 32 is inserted within the barrel of the syringe 30. A barrier layer 12 may be applied to the opposing end 32b of the plunger 32, such that the barrier layer 12 will be located between any drug product 33 and the elastomeric material 16 containing the taggant 18. By concentrating the taggant 18 within the plunger and away from the drug contact surfaces of the plunger 32, the likelihood of interaction between the taggant 18 and the drug product may be minimized or eliminated.

Various methods may be used to concentrate the taggant 18 in one portion of the plunger 32. For example, as previously described, the plunger component may be molded in multiple steps. A first elastomeric material containing the taggant may be molded into a first portion of the component, and a second material that does not contain taggant may be molded over the first portion form the complete component. Alternatively, the taggants may be dispersed in a mold release fluid that is sprayed in a mold prior to introducing the elastomeric material into the mold, as described in detail above. The result would be that the taggants are embedded on and/or near the surface of the molded component.

In order to ensure that the taggants are confined to specific surfaces or portions of the molded component, multiple mold release formulations may be prepared and applied to the mold. For example, for forming of the plunger 32, a first mold release fluid containing the taggants may be applied to the surface of the mold cavity corresponding to the distal surface 32a of the plunger 32, while the surface of the mold cavity corresponding to the opposing end surface 32b of the plunger 32 and the surfaces of the mold cavity corresponding to the circumferential side of the plunger 32 may be sprayed with a second mold release fluid that does not contain taggants, such that the taggants are concentrated in only the distal end 32a of the molded plunger 32.

In one embodiment, the taggant 18 is preferably a chemical taggant incorporated or embedded on the surface of the plunger 32, such that internal reflection properties may be utilized to determine the location of the plunger 32. For example, where the plunger 32 is positioned within a syringe (not shown), light may be directed into the interior of the syringe along the longitudinal axis, such that the light is trapped within the walls of the syringe barrel. The ribs of the plunger 32 essentially break or disrupt the total internal reflection and are illuminated at the interface of the plunger 32 and syringe barrel. The illumination of this interface can be used to probe the surface-surface interaction and highlight any tampering, due to the presence of the taggant layer on the surface of the plunger 32 as the plunger 32 is moved.

In another embodiment, a chemical taggant fluid is applied behind the plunger 32 to detect movement of the plunger 32. In such an embodiment, the pharmaceutical drug product contained in the syringe barrel could therefore not be administered or refilled, without disrupting the taggant fluid, which serves to highlight any tampering activities.

Referring now to FIG. 3C, a needle shield 34 is illustrated according to another embodiment of the present invention. The needle shield 34 comprises a plurality of portions 16a, 16b comprising the first elastomeric material 16 containing one or more taggants 18. For example, a first portion 16a is formed in an annular portion around the base of the needle shield 34, while the second portion 16b is formed as a portion of the tip of the needle shield 34. The remaining body 17 of the needle shield 34 comprises a second elastomeric material that does not contain any taggants. The taggants 18 in each of the first and second portions 16a, 16b may be alike or different. Similarly, the elastomeric materials in each of the first and second portions 16a, 16b, and the body 17 may be the same or different. The needle shield 34 may further include a barrier layer 12 applied to the surface of an internal cavity that houses the syringe needle (not shown) when the needle shield 34 is in an installed condition as illustrated in FIG. 3A.

The components made according to the various embodiments of the present invention may also be provided in the form of tip caps for syringes having a luer lock system, such as the embodiment illustrated in FIGS. 4A and 4B. The tip cap 44 includes a first portion comprising an elastomeric material 16 and one or more taggants 18, wherein the first portion is confined to an end of the head portion of the tip cap 44. A majority of the body of the tip cap 44 may be formed from a second elastomeric material 17 that does not contain any taggants. The body may also include an internal cavity for housing the male luer lock fitting (not shown) when the tip cap 44 is in the installed condition as illustrated in FIG. 4A. The surface of the cavity and/or the opposing end of the tip cap 44 relative to the first portion may optionally be provided with a barrier film 12.

According to the present invention, the incorporation of taggants in an elastomeric component may enable the integration of the component into a smart device. For example, a specific color plunger may be optically recognized by a smart medical device and the information would specify a dosage rate for the administration of a medicine by the smart device. In another example, a magnetic taggant may be used to determine plunger location (and consequently dosing) by various methods, such as an induction sensing mechanism. This may be advantageous for opaque syringes containing a pharmaceutical that is sensitive to light. A magnetic plunger could also be used in placement/loading of the smart device. For example, where the taggant is a magnetic material, remote sensing is possible, such that one may be able to remotely detect tampering of the plunger without seeing the plunger, even in a case of attempted removal of the plunger.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An elastomeric component for a device containing a pharmaceutical drug product, the elastomeric component having an outer drug contact surface comprising:
   a first portion comprising at least one taggant and a first elastomeric material; and
   a second portion comprising a second elastomeric material between the first portion and the outer drug contact surface,
   wherein the at least one taggant has a first diffusivity relative to the first elastomeric material and a second diffusivity relative to the second elastomeric material, and the second diffusivity is less than the first diffusivity.

2. The elastomeric component of claim 1, wherein the first portion is adjacent to the second portion.

3. The elastomeric component of claim 1, wherein the first portion comprises an elastomeric matrix, the first elastomeric material comprises a continuous phase of the elastomeric matrix, and the at least one taggant comprises a discontinuous phase of the elastomeric matrix.

4. The elastomeric component of claim 1, wherein each of the first elastomeric material and the second elastomeric material comprises a polymer independently selected from the group consisting of polyisoprene, polybutadiene, styrene-butadiene copolymers, ethylene-propylene copolymers, ethylene-propylene-diene copolymers, chlorosulphonated polyethylene, ethylene-vinyl acetate copolymer, styrene-isoprene copolymers, fluoroelastomers, butyl rubber, isoprene rubber, butadiene rubber, halogenated butyl rubber, ethylene propylene terpolymer, silicone rubber, and combinations thereof.

5. The elastomeric component of claim 4, wherein the polymer of the first elastomeric material is covalently bonded to a surface of the at least one taggant.

6. The elastomeric component of claim 1, wherein the at least one taggant is magnetic.

7. The elastomeric component of claim 1, wherein the at least one taggant is fluorescent.

8. The elastomeric component of claim 1, wherein the at least one taggant has one or more identifiable properties relative to the first elastomeric material, and the one or more identifiable properties are selected from the group consisting of particle size, particle size distribution, shape, particle shape distribution, color, isotopic composition, and combinations thereof.

9. The elastomeric component of claim 1, wherein the at least one taggant is selected from the group consisting of ceramic materials, hydrocarbon oil, fluorocarbon oils, magnetic materials, surface functionalized particulates, particulates having unique isotopic ratios, composite particles, and RFID microchips.

10. The elastomeric component of claim 1, further comprising a barrier film on at least a portion of a surface of the second portion.

11. The elastomeric component of claim 10, wherein the barrier film comprises a material selected from the group consisting of polytetrafluoroethylene (PTFE), ethylene tetrafluoroethylene (ETFE), homopolymers and copolymers of tetrafluoroethylene (TFE), perfluoroalkoxy polymer resin (PFA), copolymers of hexafluoropropylene and tetrafluoroethylene, polyethylenetetrafluoroethylene (PETFE), polyvinyl fluoride (PVF), fluorinated ethylenepropylene copolymers (FEP), polyethylenechlorotrifluoroethylene (PECTFE), polyvinylidene fluoride (PVDF), polychlorotrifluoroethylene, (PCTFE), and derivatives thereof.

12. The elastomeric component of claim 10, wherein the at least one taggant has an average particle size greater than an average pore size of the barrier film.

13. A containment system comprising:
a container containing a pharmaceutical drug product and having at least one opening; and
the elastomeric component of claim 1, the elastomeric component closing off the at least one opening.

14. The containment system of claim 13, wherein the elastomeric component is inserted in the opening, such that the second portion is positioned between the first portion and the pharmaceutical drug product.

15. The containment system of claim 13, wherein the elastomeric component is selected from the group consisting of a vial stopper, a syringe plunger, a cartridge piston, a needle shield, and a syringe tip cap.

* * * * *